ived. The new derivative is
United States Patent [19]
Okami et al.

[11] 4,426,447
[45] Jan. 17, 1984

[54] HOMOCITRIC ACID OLIGORIBOSIDE DERIVATIVE FOR PREVENTION OF DENTAL CARIES

[75] Inventors: Yoshiro Okami, Tokyo; Kazuhiko Yamada, Fujisawa; Masachika Takashio, Tokyo, all of Japan

[73] Assignee: Zaidan Hojin Biseibutsu Kagaku Kenkyu Kai, Tokyo, Japan

[21] Appl. No.: 375,924

[22] Filed: May 7, 1982

Related U.S. Application Data

[60] Division of Ser. No. 281,800, Jul. 9, 1981, which is a continuation-in-part of Ser. No. 238,324, Feb. 26, 1981, abandoned.

[30] Foreign Application Priority Data

Mar. 8, 1980 [JP] Japan ................................. 55-29690

[51] Int. Cl.³ .................. C12P 19/44; C12N 9/99; C12N 1/20; C12R 1/465

[52] U.S. Cl. ........................................ 435/74; 435/83; 435/184; 435/253; 435/886

[58] Field of Search .................... 435/74, 82, 83, 253, 435/184, 886, 72

[56] References Cited

PUBLICATIONS

Okami et al., J. Antibiot., 34(3), 344–345 (Mar. 1981).

*Primary Examiner*—Esther M. Kepplinger
*Attorney, Agent, or Firm*—David M. Morse

[57] ABSTRACT

Dextransucrase synthesis of dextran from sucrose is inhibited by a novel homocitric acid oligoriboside derivative and its nontoxic salts. The new derivative is obtained by fermentation of certain Streptomyces sp. such as Streptomyces sp. MF 980-CF1 (FERM-P5430; ATCC 31820) and is useful in the prevention of dental caries.

3 Claims, 4 Drawing Figures

HOMOCITRIC ACID OLIGORIBOSIDE DERIVATIVE FOR PREVENTION OF DENTAL CARIES

CROSS-REFERENCE TO RELATED APPLICATION

This is a division of our co-pending application Ser. No. 281,800, filed July 9, 1981 which in turn was a continuation-in-part application of co-pending application Ser. No. 238,324 filed Feb. 26, 1981, now abandoned.

BACKGROUND OF THE INVENTION

1. Field of the Invention

This invention relates to a novel homocitric acid oligoriboside derivative which inhibits dextransucrase produced by cariogenic strains of oral *Streptococcus mutans*. As an inhibitor of dextransucrase, the new derivative can be used as an anti-caries agent.

2. Description of the Prior Art

The role of *Streptococcus mutans* in dental caries is well documented. The enzyme dextransucrase (glucosyltransferase) produced by a number of strains of *Streptococcus mutans* synthesizes dextran from the sucrose passing through the mouth with foods or drinks, resulting in the formation of dental plaque and dental caries. Dental caries is the decay of teeth caused by demineralization of the enamel surface with organic acids produced by bacteria which adhere to teeth surfaces. Bacterial adherence to smooth surfaces such as teeth is mediated by the sticky insoluble dextran.

It is recognized that an effective inhibitor of dextransucrase in the mouth would be of benefit in controlling plaque formation and preventing dental caries. Various dextransucrase inhibitors have been suggested in the art, but applicants are unaware of any heretofore successful inhibitor agent for prevention of dental caries.

SUMMARY OF THE INVENTION

There is provided by the present invention a new homocitric acid oligoriboside derivative having the formula

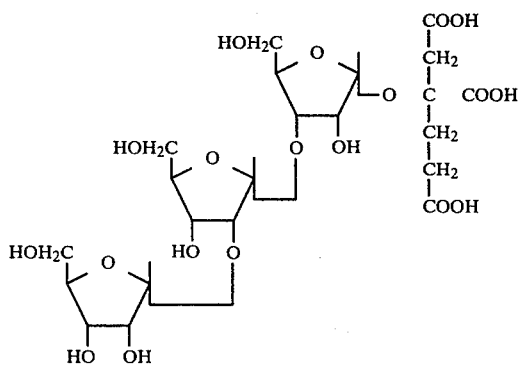

and nontoxic salts thereof. The new derivative designated herein as ribocitrin is obtained from the fermentation broth of certain ribocitrin-producing strains of Streptomyces sp., most preferably Streptomyces sp. MF 980-CF1 (FERM-P5430; ATCC 31820) or a mutant thereof.

Ribocitrin and its nontoxic salts inhibit the dextransucrase synthesis of dextran from sucrose and are thus useful for preventing dental caries. The novel derivative of the present invention and its nontoxic salts may be provided in the form of a suitable dental vehicle such as a toothpaste or powder, a mouthwash or a chewing gum.

DETAILED DESCRIPTION

Figure 1:
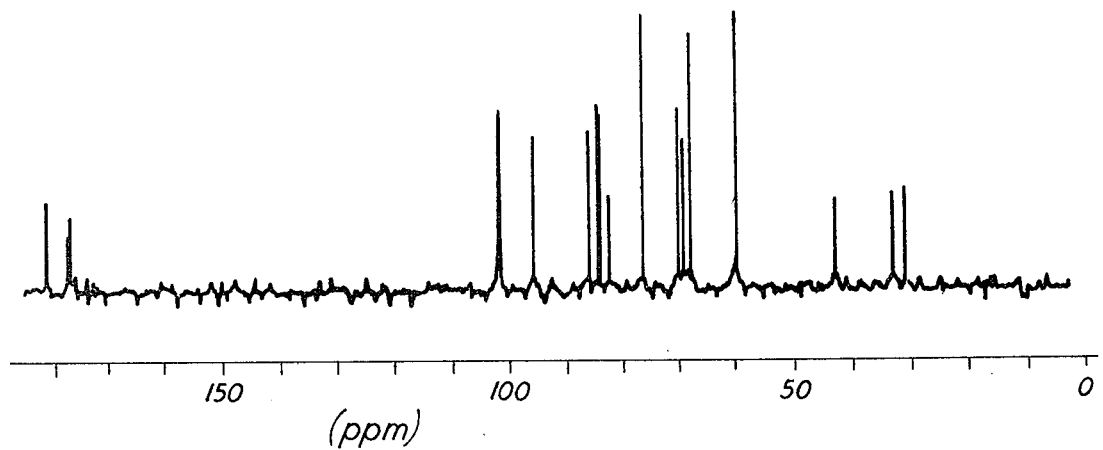
FIG. 1 shows the $^{13}C$ nuclear magnetic resonance spectrum of ribocitrin sodium salt when dissolved in $D_2O$.

Ribocitrin, the novel dextransucrase inhibitor of the present invention, is obtained from the cultured broth of certain Streptomyces organisms. Any strain of microorganism belonging to the genus Streptomyces and capable of forming ribocitrin in culture medium may be used in the fermentation. The preferred producing organisms are the novel strain Streptomyces sp. MF 980-CF1 and ribocitrin-producing mutants thereof.

Strain MF 980-CF1 was isolated from a soil sample collected around Lake Kawaguchi in Japan. A biologically pure culture of this strain was deposited with the Institute for Microbial Industry, Agency of Industrial Science and Technology, Japan, and assigned deposit number FERM-P No. 5430. Another culture was deposited with the American Type Culture Collection, Rockville, Md., U.S.A. and added to their permanent collection of microorganisms as ATCC 31820.

The cultural characteristics of strain MF 980-CF1 are as follows:

(a) Morphology

Strain MF 980-CF1 when grown well on agar media shows a linear or spiral structure of aerial mycelia elongated from simple-branched, well-elongated substrate mycelia. When matured, spore chains of 10–50 cylindrical spores ($0.8 \times 1.8$ μm) are formed on top of the mycelia. Observations by electron microscopy reveal smooth surface spores with no spiny or hairy structure on the spores. Neither flagella nor sporangia are observed. Consequently, the strain can be classified as a typical Streptomyces species.

(b) Characteristics on Various Media (1) Sucrose-nitrate agar (27° C. incubation): White (white a) and poor aerial mycelia are formed above the substrate growth of yellowish brown color (2db extra pastel series for hue-Color Harmny Manual). No distinctive diffusible pigments are formed in the medium.

(2) Glycerol-Asparagine Agar (27° C. incubation): Substrate growth shows weak reddish-brownish (5 lg, hue 5) color. White aerial mycelia first appear on the peripheral parts of the colony and gradually cover the whole parts. No distinctive soluble pigments are formed.

(3) Starch Agar (27° C. incubation): Brownish-white (5 ba, near gray series) aerial mycelia are formed above the orange (4 pe, hue 4) colored substrate growth. No distinctive soluble pigments are formed.

(4) Tyrosine Agar (27° C. incubation): Substrate growth shows reddish-brown (5 lg, hue 5) color. White (white a) aerial mycelia are formed on the peripheral part of the colony. Melanoid pigment is formed.

(5) Nutrient Agar (27° C. incubation): Growth is poor and shows no distinctive color. Aerial mycelium formation is also very poor.

(6) Yeast-Malt Agar (27° C. incubation): Grayish-white aerial mycelia are formed above the brown (chm 6 ng, hue 6) substrate growth and gradually turn to purplishgray (chm 5 dc near gray series). Brownish melanoid pigment is formed.

(7) Oat Meal Agar (27° C. incubation): Brownish-gray (chm 13 fe near gray series) aerial mycelia are formed above the reddish-orange (chm 5 le hue 5) colored substrate growth. No distinctive soluble pigment is formed.

(c) Physiological properties (1) Temperature range for growth is 14°–33° C.
(2) Starch is hydrolysed on starch agar.
(3) Skim milk is peptonized but not coagulated.
(4) Melanoid pigment is formed in tyrosine agar, yeast-malt agar and peptone-yeast-iron agar media.
(5) Nitrate is reduced.
(6) Gelatin is not liquefied.

(d) Utilization of Carbon Sources (Pridham and Gottlieb medium)

D-Glucose, L-arabinose, sucrose, D-xylose, inositol, mannitol, D-fructose and L-rhamnose are utilized, but raffinose is not.

The above properties show that this strain typically belongs to the genus Streptomyces with characteristics such as formation of spiral structure on its aerial mycelia and formation of melanoid pigment.

The properties of strain MF 980-CF1 resemble those of the following species, but there are some differences as noted below.

(1) *Streptomyces griseoaurantiacus:* Lack of melanoid pigment formation and very poor utilization of sucrose differ from properties of strain MF 980-CF1.

(2) *Streptomyces resistomycificus:* Lack of pigment formation, utilization of raffinose and pH dependence of pigment color of substrate growth differ from properties of strain MF 980-CF1.

(3) *Streptomyces diastochromogenes:* Lack of pigment formation on yeast-malt agar medium and utilization of raffinose indicate a difference between this species and strain MF 980-CF1.

(4) *Streptomyces galbus:* Pigment formation on glycerol-asparagine agar, starch agar and oatmeal agar and very poor utilization of sucrose and rhamnose differ from properties of strain MF 980-CF1.

(5) *Streptomyces neyagawaensis:* Pigment formation on glycerol-asparagine agar, starch agar and oatmeal agar and utilization of raffinose differ from properties of strain MF 980-CF1.

(6) *Streptomyces bottoropensis:* Pigment formation on glycerol-asparagine agar and utilization of raffinose differ from properties of MF 980-CF1.

Since there is no known species showing the characteristics of this stain in the genus Streptomyces, the species of MF 980-CF1 is concluded to be novel and the strain is designated herein as Streptomyces sp. MF 980-CF1.

It is to be understood that while the present invention is described in detail with reference to the strain Streptomyces sp. MF 980-CF1, it is not limited to this particular microorganism or to microorganisms fully described by the cultural characteristics disclosed herein. As with other strains of Streptomyces species, the preferred strain may be mutated artificially or spontaneously with mutagens such as ultraviolet rays, x-rays or chemical reagents. All such ribocitrin-producing mutants thus obtained are specifically intended to be included within the scope of the present invention.

Ribocitrin may be obtained using conventional fermentation methods by cultivating a ribocitrin-producing strain of the genus Streptomyces, preferably Streptomyces sp. MF 980-CF1 (FERM-P5430;ATCC 31820) or a mutant thereof, under submerged aerobic conditions in an aqueous nutrient medium. The producing organism is grown in a conventional nutrient medium containing an assimilable carbon source, e.g. carbohydrates such as glycerol, glucose, maltose, sucrose, lactose, starch or dextrin and an assimilable nitrogen source, e.g. soybean meal, peanut meal, cotton seed meal, dry yeast, peptone, meat extract, casein, corn steep liquor, nitrate nitrogen or ammonia nitrogen. Preferred carbon sources are maltose or potato stach and preferred nitrogen sources are cotton seed meal or corn steep liquor. If necessary, there may also be employed inorganic ions such as magnesium, manganese, sodium, potassium, iron, calcium, chloride, phosphate or sulfate and organic microelements such as vitamins and/or amino acids.

Production of ribocitrin can be carried out at any temperature conducive to satisfactory growth of the producing organism. Preferred incubation temperatures are from about 25° C. to 30° C. For preparation of relatively small amounts, shake flasks and surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermenting medium. Further agitation in tanks is provided by a mechanical impeller. Antifoaming agents such as lard oil may be added as needed. Incubation of the culture is continued until the desired ribocitrin substance is sufficiently accumulated in the cultured broth. Ordinarily, optimum production is achieved in from about 2 to 7 days.

After production of ribocitrin in the culture medium, the ribocitrin may be recovered therefrom by conventional isolation procedures used for water-soluble acidic substances. Advantageously, basic anion exchangers are used to adsorb the ribocitrin from the fermentation broth. Examples of suitable anion exchangers are AMBERLITE CG 400 or CG-4B ("AMBERLITE" is a trademark of Rohm & Haas Co., Philadelphia, Pa., U.S.A.), DIAION PA 316 or WA 30 ("DIAION" is a trademark of Mitsubishi Chemical Industries, Japan) and DEAE SEPHADEX ("SEPHADEX" is a trademark of Pharmacia, Uppsula, Sweden). Such anion exchangers may be in the $OH^-$, $Cl^-$ or $HCO_3^-$ form or mixtures of such forms.

After washing the adsorbent with water, the adsorbed ribocitrin is eluted in good yield with a solution of sodium hydroxide, ammonium bicarbonate or mineral salts. Preferably, sodium chloride (0.1–1 M) or ammonium bicarbonate (0.1–1 M) are employed as eluents.

Since ribocitrin is not significantly adsorbed to cation exchangers, such exchangers may be used to remove basic impurities from the ribocitrin obtained from anion exchange chromatography.

Further purification of ribocitrin may be achieved by thin layer chromatography on cellulose ("AVICEL") plates using as the developer a mixed solvent consisting of n-propanol: 3 M ammonium hydroxide (55:45 v/v) ($R_f$=0.65). Based on this, effective large scale purification of ribocitrin may be achieved by employing cellulose column chromatography with the abovementioned thin layer solvents or related solvents.

Ribocitrin being an acidic substance readily forms cationic salts with bases. Such salts may be recovered directly from the above-mentioned isolation procedure when basic solvents are used, e.g. sodium hydroxide, ammonium bicarbonate, etc., or the free acid form of ribocitrin may be converted to a desired salt by conventional salt-forming techniques. For use as an oral anti-caries agent, such salts would of course have to be nontoxic. Examples of suitable nontoxic salts include sodium, lithium, ammonium, etc.

Characterization of Ribocitrin

Figure 2:
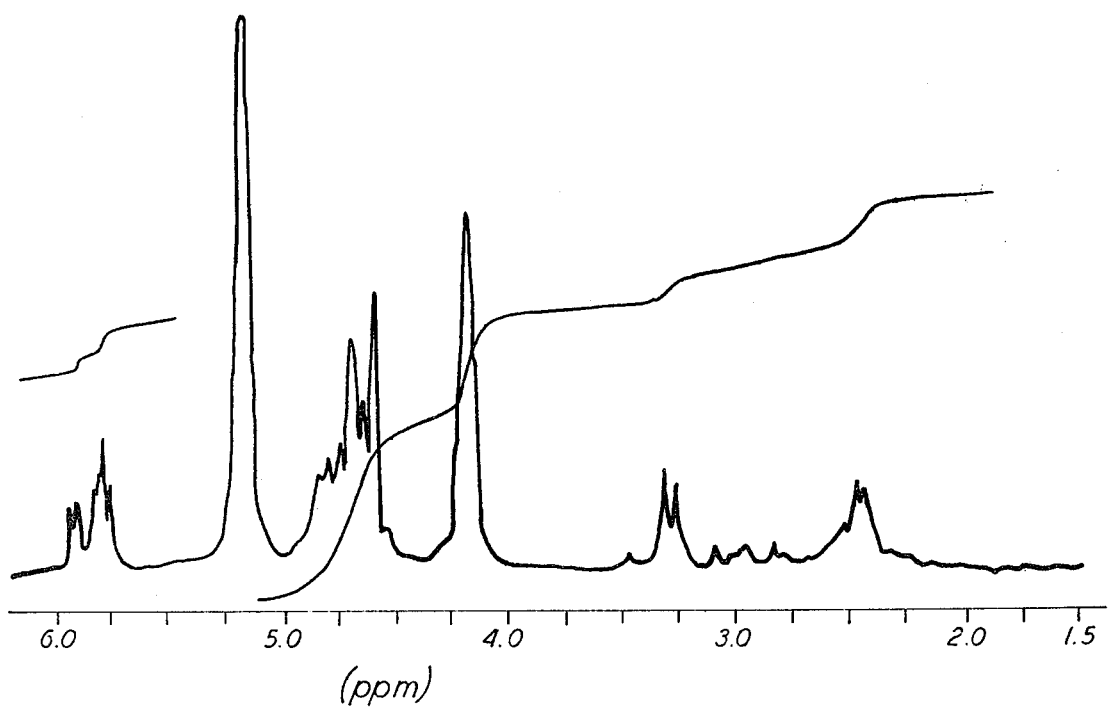
FIG. 2 shows the proton magnetic resonance spectrum of ribocitrin sodium salt when dissolved in $D_2O$.
Figure 3:
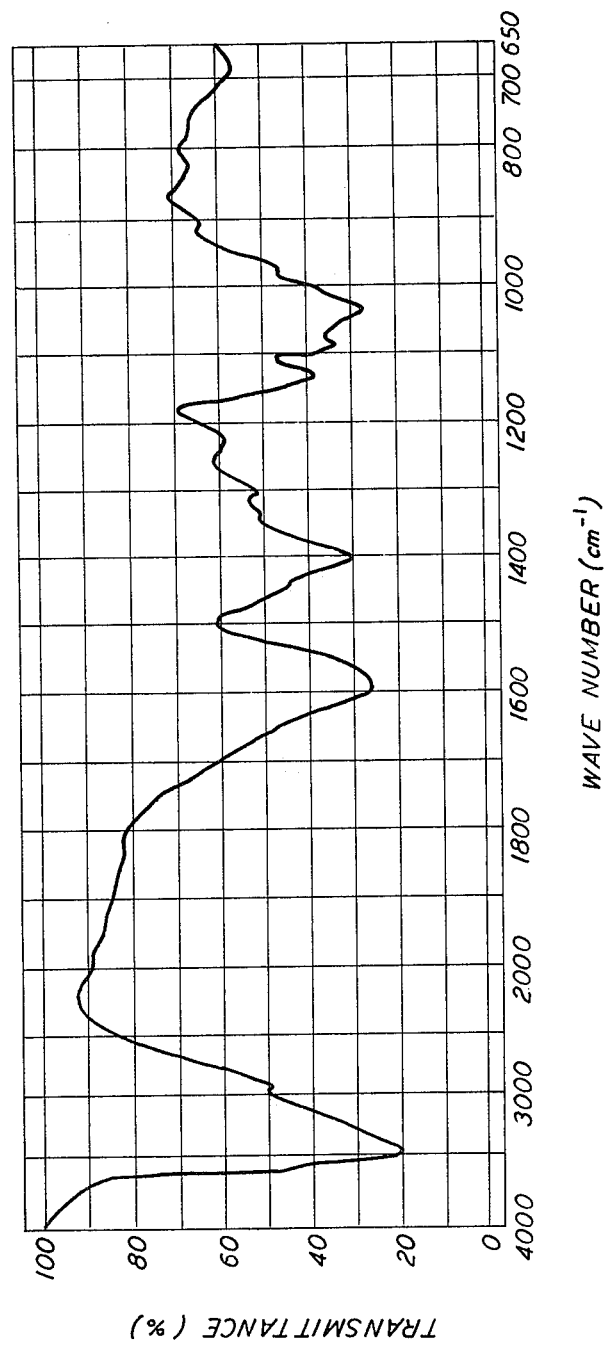
FIG. 3 shows the infrared absorption spectrum of ribocitrin sodium salt when pelleted in potassium bromide.

Ribocitrin in the form of its sodium salt has the following characterizing properties:
1. White powder, m.p. 205°–210° C. (dec).
2. Soluble in water; insoluble in organic solvents.
3. Hydrolysis or ribocitrin gives riboses and homocitric acid.
4. Elemental analysis; Found: C 40.15, H 5.31%; Calc'd for $C_{22}H_{31}O_{19}Li_3.2H_2O$:C 40.24, H 5.33%.
5. UV spectrum has no maximum.
6. Positive color reaction with phenol-sulfuric acid and orcinol hydrochloride. Negative color reaction with ninhydrin, Nelson-Somogyi reagent and diphenylamine-sulfuric acid.
7. $^{13}C$ NMR spectrum in $D_2O$ as in FIG. 1.
8. $^1H$ NMR spectrum in $D_2O$ as in FIG. 2.
9. IR spectrum (KBr disc) as in FIG. 3.

Early characterization data indicated that the partial structure of ribocitrin was as shown below:

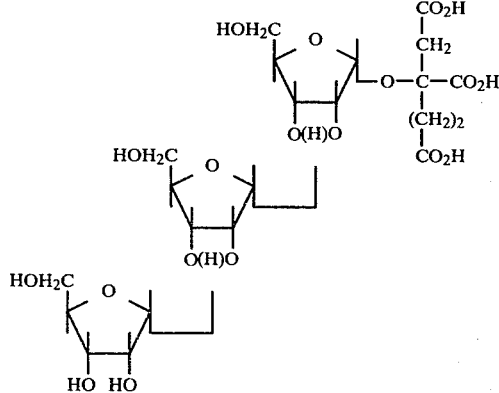

wherein each blycoside linkage between ribose moieties is a ribosyl-(1→2)-ribosyl or ribosyl-(1→3)-ribosyl bond. Additional studies confirmed that the trisaccharide moiety of ribocitrin was O-D-ribofuranosyl-(1→2)-O-D-ribofuranosyl)-(1→3)-D-ribofuranose. From extensive structural elucidation work, ribocitrin has been identified as 2-(S)-[O-α-D-ribofuranosyl-(1→2)-O-α-D-ribofuranosyl-(1→3)-α-D-ribofuranosyloxy]-1,2,4-butanetricarboxylic acid having the structural formula

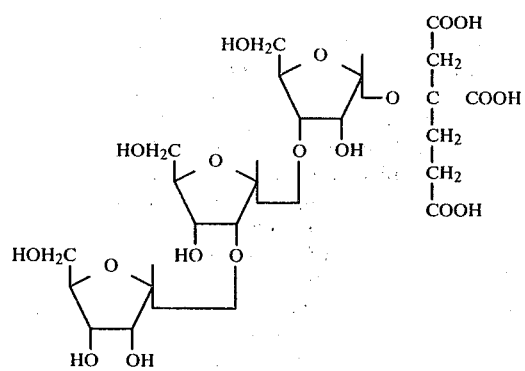

As noted above, ribocitrin and its nontoxic salts have been found to be effective inhibitors of dextransucrase in the mouth. Accordingly, synthesis of dextran from sucrose present in the oral cavity is prevented or inhibited and the dental plaque and/or dental caries resulting therefrom also controlled or prevented. The inhibitory activity of ribocitrin toward dextransucrase is demonstrated by the experiments described in Examples 2 and 3 below.

The present invention, then, provides the novel substance ribocitrin and its nontoxic salts and the process of producing ribocitrin by fermentation of certain strains of Streptomyces sp.. Additionally, there is provided a method of preventing dental caries and/or dental plaque which comprises orally administering an effective dextransucrase-inhibiting amount of ribocitrin or a nontoxic salt thereof. Finally, the present invention provides an oral composition for caries prophylaxis comprising a carrier for use in the oral cavity in combination with an effective dextransucrase-inhibiting amount of ribocitrin or a nontoxic salt thereof.

For prevention or control of dental plaque and/or dental caries, it is preferred to combine the ribocitrin or nontoxic salt thereof of the present invention with a suitable carrier. The carrier may be any conventional carrier suitable for use in the oral cavity. Thus, the carrier may be water in which case the ribocitrin or salt thereof is employed as an aqueous solution. Preferably, however, the ribocitrin or salt thereof is added to a mouthwash, a toothpaste or toothpowder, a chewing gum or to a foodstuff such as soft drinks or candy.

The following examples are provided for illustrative purposes only and are not intended to limit the scope of the invention.

EXAMPLE 1

Preparation of Ribocitrin

The strain Streptomyces sp. MF 980-CF1 (FERM-P5430) grown on a slant agar medium was used to inoculate a fermentation medium composed of 1% maltose, 1% corn steep liquor and 1% PHARMAMEDIA ("PHARMAMEDIA" is a trademark of Traders Oil Mill Co.; cottonseed meal), (pH 6.2, 125 ml in 500 ml Sakaguchi flask). The culture was incubated with shaking at 27° C. for 5 days to produce ribocitrin in the cultured broth.

To recover the ribocitrin, the pH of the combined fermented broth (5 l) was adjusted to pH 8.0 with sodium hydroxide and the fermented broth was heat treated (60° C., 30 min) and filtered. The obtained filtrate (4.5 l) was then passed through a column of DI-AION PA 316 (OH$^-$form, 1.3 l, Mitsubishi Chemical Industries Co.), and the column was washed with 10 l of water. The adsorbed ribocitrin was eluted from the column with 1 M ammonium bicarbonate. The combined active fractions (1 l, yield 83%) were concentrated to 80 ml under reduced pressure. The concentrate was then subjected to gel filtration on SEPHADEX G-15 (1 l, Pharmacia Co.) using water as the eluting solvent. Each 50 ml fraction was collected. The activity was found in fraction numbers 11-15. The combined active fraction (yield 72%) was directly applied to a DEAE-SEPHADEX A-25 column (HCO$_3^-$form, 400 ml, Pharmacia Co.) and eluted with a linear gradient of 0.1-0.7 M ammonium bicarbonate. The activity was found in ∼ the 0.25 M ammonium bicarbonate fractions. The active fractions were combined (yield 64%) and the ammonium bicarbonate was removed under reduced pressure. The concentrate thus obtained was applied successively to DEAE-SEPHADEX A-25 (Cl$^-$form, 200 ml, Pharmacia Co.) and eluted with a linear gradient of 0.01 M-0.5 M sodium chloride. The activity (yield 58%) was found in ∼ the 0.17 M sodium chloride fractions. The active fractions were combined and concentrated to 1 ml. and then desalted by a long column of SEPHADEX G-15 (30 ml) with water as the eluting solvent (166 mg, yield 55%). After chromatography with silica gel (Silic-AR CC-7, Mallinckrodt Co.) using the mixed solvent n-propanol: 3 M ammonium hydroxide (70:30 v/v), white crystals of ribocitrin sodium salt were obtained (90 mg, 49% yield).

EXAMPLE 2

Demonstration of Inhibitory Activity to Dextransucrase

Dextransucrase was prepared as follows: *Streptococcus mutans* ATCC 27607 was inoculated to Brain Heart Infusion bouillon (Eiken Chemical Co.) and grown overnight at 37° C. The culture supernatant obtained by centrifugation was precipitated with ammonium sulfate at 50% saturation. The precipitated enzyme was desalted and purified by conventional procedures. Inhibitory activity to dextransucrase was assayed as follows: 2.7 ml of substrate solution (0.3% sucrose, 0.04% sodium azide, 30 mM potassium chloride, 30 mM sodium chloride in 50 mM imidazole-HCl buffer (pH 6.8), 0.3 ml of the test solution or water as control, and 50 μl of dextransucrase were mixed. After incubation at 37° C. for 14 hours, the turbidity at 600 nm was measured against water as blank, and the percent inhibition was calculated from the following equation:

$$\text{Percent inhibition} = \frac{(\text{Turbidity of control}) - (\text{Turbidity of test})}{(\text{Turbidity of control})} \times 100$$

Figure 4:
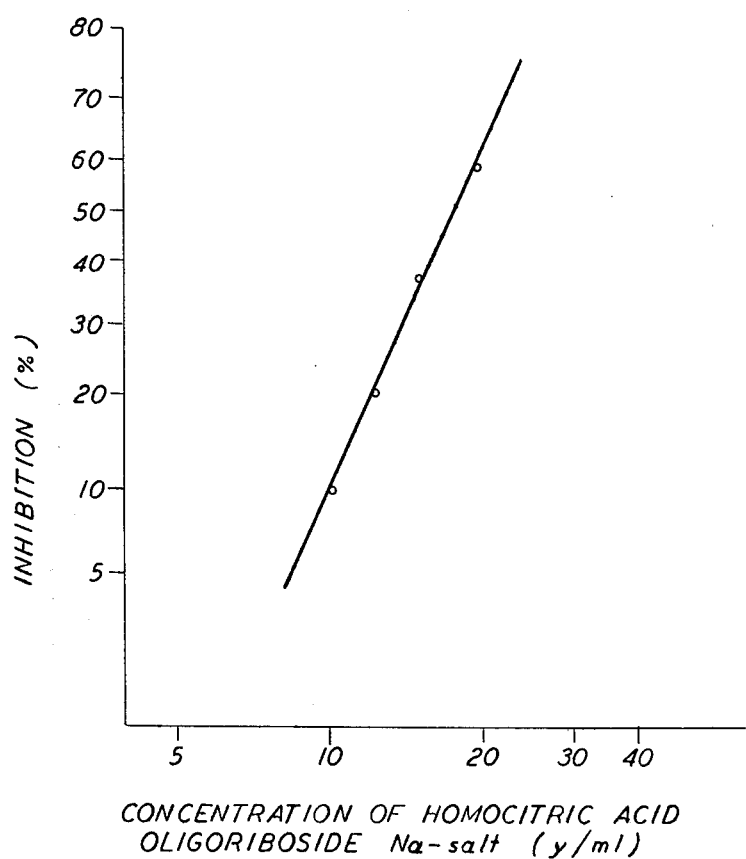
FIG. 4 shows the relationship between the concentration of ribocitrin sodium salt and the inhibition ratio (%) to dextransucrase activity.

The definition of 1 unit of this material is the amount which gives 50% inhibition. FIG. 4 shows the relationship between the concentration of ribocitrin and the percent inhibition determined by the assay method described above.

EXAMPLE 3

Demonstration of *Streptococcus mutans* Adherence

Heart Infusion bouillon (Difco) containing various concentrations of sucrose was autoclaved and added aseptically with various amounts of ribocitrin aqueous solution (filter-sterilized) or sterile water for control (final volume is 3.0 ml and final concentrations are shown in Table 1). Each tube was inoculated with $1 \times 10^5$ CFU of *Streptococcus mutans* ATCC 27607 grown overnight at 37° C. in Brain Heart Infusion bouillon (Difco) and incubated anaerobically in a candle jar at 37° C. for 14 hours. The tube was positioned at an angle 30° from the horizontal. Nonadherent cells were removed by pouring off the broth and the test tube was washed three times with 3 ml of 5 mM phosphate buffer (pH 6.0). The adhered plaque (insoluble dextran and cellular aggregates formed as a result of insoluble dextran production) was suspended in 3 ml of phosphate buffer described above by mechanical stirring and by scraping the surface with a glass rod. Turbidity of the suspension was measured at 600 nm. The results are shown in Table 1 below.

TABLE 1

| | Inhibition of *Streptococcus mutans* Adherence | | | | | |
|---|---|---|---|---|---|---|
| | Concentration (%) of sucrose | | | | | |
| | 0.5 | | 1.0 | | 2.0 | |
| Concentration (μg/ml) of Ribocitrin (sodium salt) | Turbidity (600 nm) | Percent inhibition | Turbidity (600 nm) | Percent inhibition | Turbidity (600 nm) | Percent inhibition |
| 0 | 0.617 | — | 0.595 | — | 0.502 | — |
| 50 | 0.510 | 17 | 0.340 | 43 | 0.333 | 33 |
| 100 | 0.249 | 60 | 0.173 | 71 | 0.132 | 73 |

We claim:

1. A process for the production of ribocitrin or a nontoxic salt thereof which comprises cultivating the ribocitrin-producing strain Streptomyces sp. MF980-CF1 (FERM-P5430; ATCC 31820) or a ribocitrin-producing mutant thereof under submerged aerobic conditions in an aqueous nutrient medium until a substantial amount of ribocitrin is produced by said organism in said culture medium and recovering the ribocitrin or nontoxic salt thereof from the medium.

2. The process according to claim 1 which includes the additional step of converting ribocitrin to a nontoxic salt thereof.

3. A biologically pure culture of the microorganism Streptomyces sp. MF 980-CF1 (FERM-P5430; ATCC 31820), said culture being capable of producing ribocitrin in a recoverable quantity upon cultivation in an aqueous nutrient medium containing assimilable sources of carbon and nitrogen.

* * * * *